US006212939B1

(12) United States Patent
Thundat

(10) Patent No.: US 6,212,939 B1
(45) Date of Patent: Apr. 10, 2001

(54) UNCOATED MICROCANTILEVERS AS CHEMICAL SENSORS

(75) Inventor: Thomas G. Thundat, Knoxville, TN (US)

(73) Assignee: Lockheed Martin Energy Research Corporation, Oak Ridge, TN (US)

(*) Notice: Subject to any disclaimer, the term of this patent is extended or adjusted under 35 U.S.C. 154(b) by 0 days.

(21) Appl. No.: 09/405,473

(22) Filed: Sep. 24, 1999

(51) Int. Cl.$^7$ ................................................. G01N 37/00
(52) U.S. Cl. ........................ 73/24.02; 73/23.2; 73/32.05; 250/370.01; 422/88
(58) Field of Search ........................... 73/240.02, 23.2, 73/24.06, 35.16, 35.14, 31.02, 31.05, 28.02, 31.06; 250/306, 307, 370.01, 234; 422/88, 91, 83; 310/311, 330

(56) References Cited

U.S. PATENT DOCUMENTS

| | | | |
|---|---|---|---|
| 4,094,608 | * | 6/1978 | Young ................................. 73/24.02 |
| 4,942,299 | * | 7/1990 | Kazmerski .......................... 250/306 |
| 5,161,147 | * | 11/1992 | Goldberg et al. .................. 250/307 |
| 5,440,008 | * | 8/1995 | Wachter et al. . |
| 5,464,977 | * | 11/1995 | Nakagiri et al. .................... 250/306 |
| 5,719,324 | * | 2/1998 | Thundat et al. . |
| 5,770,856 | * | 6/1998 | Fillard et al. ....................... 250/234 |
| 5,918,263 | * | 6/1999 | Thundat ............................. 73/35.16 |
| 5,977,544 | * | 11/1999 | Datskos et al. ................. 250/370.01 |

OTHER PUBLICATIONS

Albrecht et al. Journal of Vacuum Science and Technology A 8 3386 (1990), Microfabrication of Cantilever Styli for the Atomic Force Microscope.*
Thundat et al. Microscale Thermophysical Engineering 1:185–199 (1997), Microcantilever Senors.*
Scott et al., Academic Press 1975, Surface Physics of Phosphors and Semiconductors, pp. v–xiv and pp. 162–175.*

* cited by examiner

Primary Examiner—Daniel S. Larkin
Assistant Examiner—Michael Cygan
(74) Attorney, Agent, or Firm—Hardaway/Mann IP Group of Nexsen Pruet Jacobs & Pollard, LLC

(57) ABSTRACT

A method and device are provided for chemical sensing using cantilevers that do not use chemically deposited, chemically specific layers. This novel device utilizes the adsorption-induced variation in the surfaces states on a cantilever. The methodology involves exciting charge carriers into or out of the surface states with photons having increasing discrete levels of energy. The excitation energy is provided as discrete levels of photon energy by scanning the wavelength of an exciting source that is illuminating the cantilever surface. When the charge carriers are excited into or out of the surface states, the cantilever bending changes due to changes in surface stress. The amount of cantilever bending with respect to an identical cantilever as a function of excitation energy is used to determine the energy levels associated with adsorbates.

12 Claims, 3 Drawing Sheets

UNCOATED MICROCANTILEVERS AS CHEMICAL SENSORS

This invention was made with Government support under Contract No. DE-AC05-96OR22464 awarded by the U.S. Department of Energy to Lockheed Martin Energy Research Corporation, and the U.S. Government has certain rights in this invention.

BACKGROUND OF THE INVENTION

1. Field of the Invention

This invention relates to the field of chemical detection using cantilevered microelectromechanical structures (MEMS) devices and particularly to methods for detecting specific chemical entities using uncoated cantilevers by analysis of selectively excited adsorption-induced surface states upon exposure to photons having discreet energy levels.

2. Prior Art

The microcantilever sensor is a simple sensor concept with extreme high mass sensitivity or surface stress sensitivity. A sensitivity of sub-picograms has been demonstrated for microcantilever sensors and there exists the potential of achieving a mass sensitivity in the range of sub-femtograms. These microcantilevers can be made with a length ranging from one micron to a few hundred microns. The microcantilever resonance frequency changes due to adsorption-induced mass loading. The cantilever can also undergo bending due to adsorption-induced surface stress variation if the adsorption is confined to a single surface. The extreme mass sensitivity of the microcantilever is due primarily to its own extremely small mass. Microcantilever sensors based on mass detection were discussed in U.S. Pat. No. 5,445,008 to Wachter and Thundat. Microcantilever chemical sensors based on variation surface stress is discussed by Thundat and Wachter in U.S. Pat. No. 5,719,324.

The primary disadvantage to using microcantilevers, as well as other forms of mass sensor such as quartz crystal microbalances, surface acoustic wave devices, plate wave resonators, Lamb and Love wave sensors, is the inability to distinguish different chemical entities. As a result, to direct adsorption to a single surface, it has been known to apply coatings of various types to the cantilever. For example, coating the surface of a mass sensor with a thin layer of gold makes the sensor sensitive to mercury adsorption, but not selective because it also becomes sensitive to hydrogen sulfide and other sulfur compounds. Filters and other fixes to attain greater selectivity detract from the primary advantages of microcantilevers, small size and simplicity.

An alternative approach to chemical sensing is the use of arrays of mass sensors wherein each element is coated with a chemical coating selected to produce an unique and characteristic response. This requires many sensor elements and different chemical coatings. This also requires the use of neural networks for correct computation. Finding chemicals and unique combination of chemicals that can act as chemically selective or partially selective coatings is time consuming. Reliably applying the coatings to miniature sensors can be a challenging problem. Moreover, in a micromachined array, it is difficult to make all the individual cantilevers identical. Finally, the sensing based on a chemically modified single cantilever may not be reliable or reproducible due to a number of reasons including contamination. Therefore, chemical sensors based on chemically selective coatings do not offer a clear path to the development of reliable sensors that are miniature, easy to mass produce, and reliable.

BRIEF DESCRIPTION OF THE INVENTION

It is a first object of this invention to provide a method for detecting individual chemical species using uncoated microcantilevers.

It is a further object of this invention to utilize the chemistry of the cantilever itself as a principal determinant of selectivity.

It is a further object of this invention to use differences in the frequency of light as a discriminator in determining the identity of chemicals which are adsorbed on the surface of a cantilever.

These and other objects may be achieved by selecting an array of microcantilevers formed from semiconductor materials selected to have different band gaps and measuring the change in position of the cantilevers in the presence of one or more chemical entities while the surface structure of the cantilever is being scanned over a range of wavelengths of light lower than the band gap of at least one semiconductor cantilever in the array.

The invention may be used as the basis for a laboratory analytical instrument in the form of a spectrophotometer. It may be used industrially for process control. It may be used for environmental monitoring as a highly portable field instrument. Finally, its small size and low power requirement make the invention especially suitable as a personal warning device for soldiers potentially exposed to chemical and biological warfare agents.

DETAILED DESCRIPTION OF THE INVENTION

Because the surface of any material is an abrupt interruption, all the surfaces have electronic surface states called intrinsic surface states. These are basically broken bonds. For example, in a covalent material the surface atoms are unable to complete the covalent bond due to the lack of neighbors. Conceptually, there is only one electron in the covalent bond sticking out of the surface. These broken covalent bonds are often referred to as dangling bonds. The dangling bonds give rise to localized energy states at the surface and are distinguishable from the energy states in the mass of the material. Choice of material is important. For example, on a silicon surface the intrinsic surface states lies in the band gap. In the case of compound semiconductors the surface states lie typically outside the band gap.

On compound semiconductors, these surface states can occur within the band gap. These surface states are usually distributed continuously within the band gap and may be filled to a certain level (neutral level) making the surface electrically neutral. These levels can act as acceptors or donors depending on whether they are filled or empty. The position of the neutral level is such that the surface states are occupied up to the neutral level. The states below the neutral levels are donor-like because they are neutral when occupied and are positive (holes) when empty. The levels above the neutral level act as acceptor levels.

Adsorption of foreign atoms or molecules on the surface modifies the distribution of the surface states by completing the broken bonds. Adsorbed species can also introduce foreign surface states (extrinsic surface states). The surface state energy associated with the adsorbate species depends on the type of bond (or interaction) it forms with the surface. Therefore, a microcantilever surface with an adsorbed species is different in its surface electronic energy distribution as compared to a reference surface.

The following are the band gaps of common semiconductors.

Ge=0.7 eV
Si=1.12
GaAs=1.42 eV
CdSe=1.7
CdS=2.4
GaP=2.3
SiC=3
ZnO=3.2
TiO2=3.2
SnO2=3.8

Figure 1:
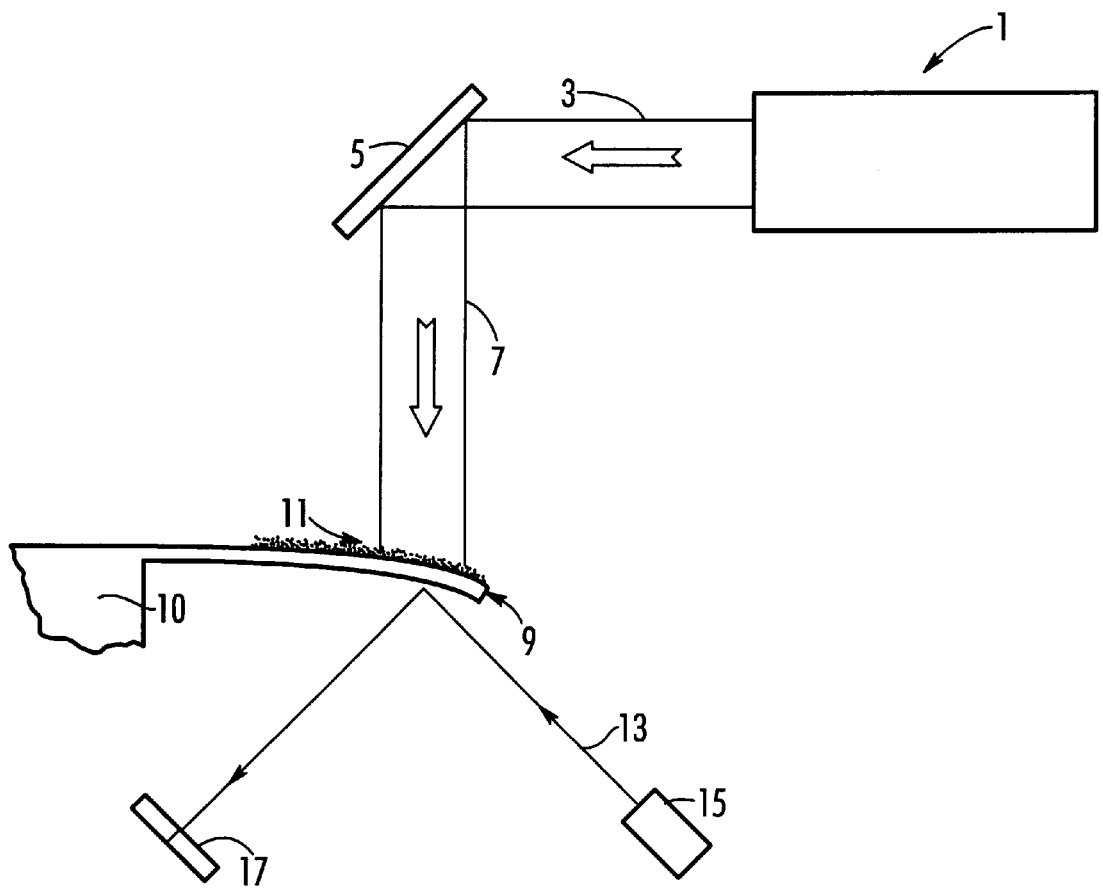
FIG. 1 is a schematic drawing of the components used in the practice of the invention.
Figure 2:
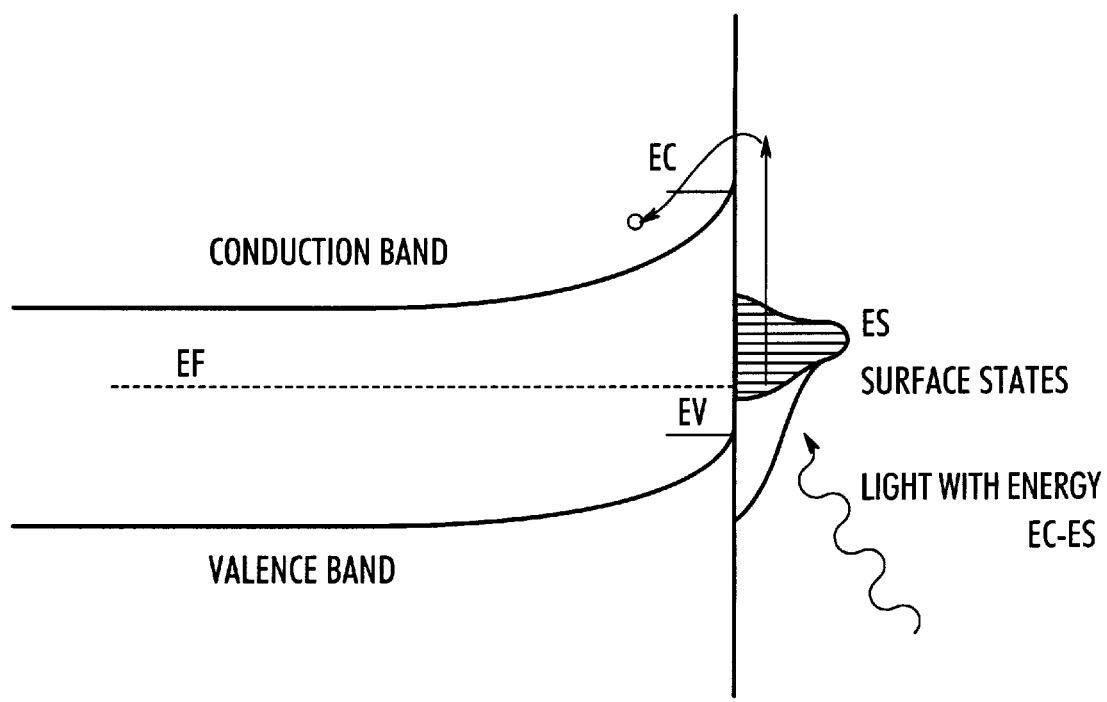
FIG. 2 is an energy band diagram of a semiconductor surface with adsorption-induced surface states.
Figure 3:
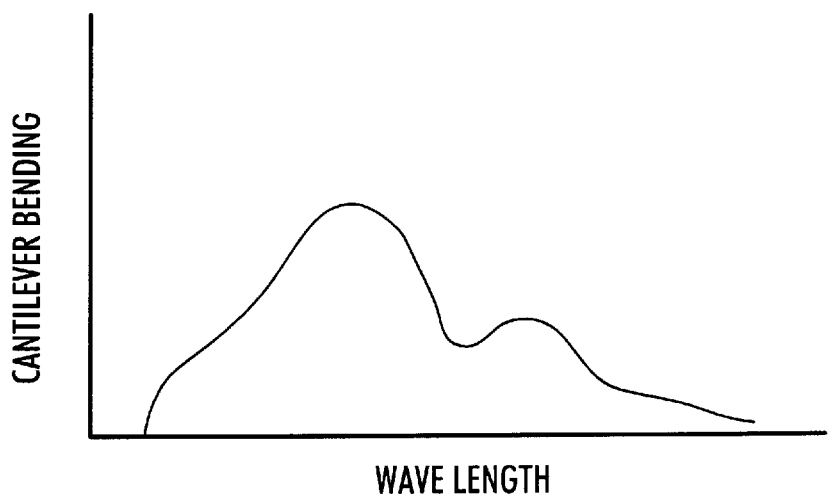
FIG. 3 is a graph of cantilever bending vs. wave length of the light shown on the surface of the microcantilever.

The present invention utilizes a new method of achieving chemical selectivity. This method utilizes optical manipulation of charge carriers in the surface states of a semiconducting cantilever surface. The method is based on the fact that surface state density is altered by adsorption of chemicals on the surface of a semiconductor substrate and the alteration in the surface state density in the energy diagram is unique to a semiconductor-analyte pair. The method involves manipulation by populating or depopulating the surface state on these semiconductor surfaces by projection photons onto the covered surface. This is carried out by illuminating or irradiating the semiconductor surface with photons at incrementally small changes of energy. The apparatus for the method is shown in FIG. 1. The energy of the photon is selected in such a way that there will not be any band to band transition, i.e., lower than the band gap of the chosen semiconductor. Due to illumination, charge carriers move from band to the surface states or surface state to a band as shown in FIG. 2. Populating or depopulating the surface states changes the charged nature of the semiconductor surface. Because the semiconductor surface is in the form of a cantilever, changes in surface charge on one of the surfaces creates a differential mechanical stress that deflects the cantilever. Therefore, the populating or depopulating of the surface states appears as mechanical bending of the cantilever element. A plot of the bending of the cantilever as a function of photon energy will have peaks corresponding to the position of the surface states as shown in FIG. 3. A differential bending of a cantilever having surface adsorbates with respect to a reference cantilever will be unique to the analyte-substrate pair.

Figure 4:
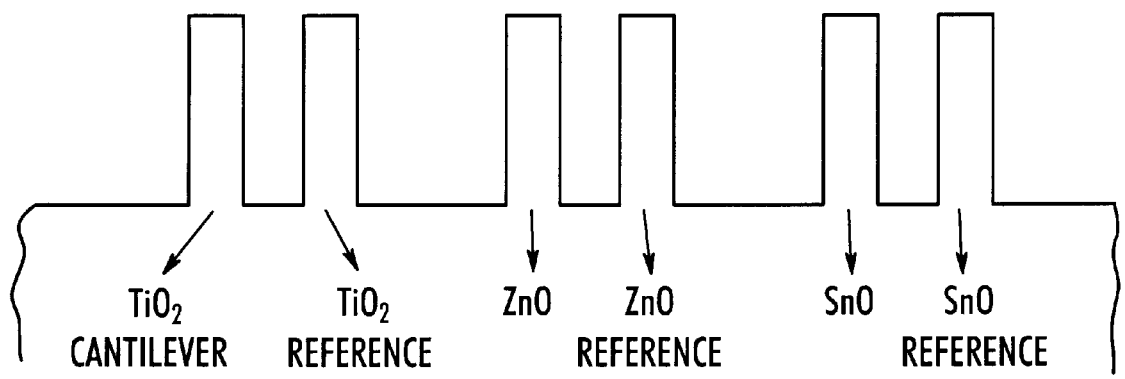
FIG. 4 is block diagram of an array of cantilevers

This invention further contemplates a sensor device consisting of an array of cantilevers with each cantilever element made of different semiconductor as shown in FIG. 4. Using a number of substrate semiconductor materials the analyte can be identified using the unique energy level occupied by the analyte on the semiconductor. This concept of cantilever array also allows the identification of mixtures of analytes.

This invention further contemplates a sensor device that can respond to analytes at higher speed using chopped light with incremental change in energy. The cantilever bends due to variation in the surface state population. As the carriers move away from the surface the cantilever returns to equilibrium position. As the cantilever is exposed to incremental changes in the photon energy, the cantilever goes into vibration with amplitudes increasing with increasing population or depopulation. Therefore by measuring the amplitude of cantilever oscillation as a function of energy of the incident photon, a map of the surface states can be obtained. If there is a very poor communication between the surface states and the bulk of the cantilever the charge carriers may not be able to depopulate rapidly. This can be overcome by using a purging pulse of photons of higher energy immediately following the irradiation with photons of changing energy. The energy of this second pulse is such that it can impart enough energy to the charge carriers in the surface to make them move into conduction or valence bands.

Figure 5:
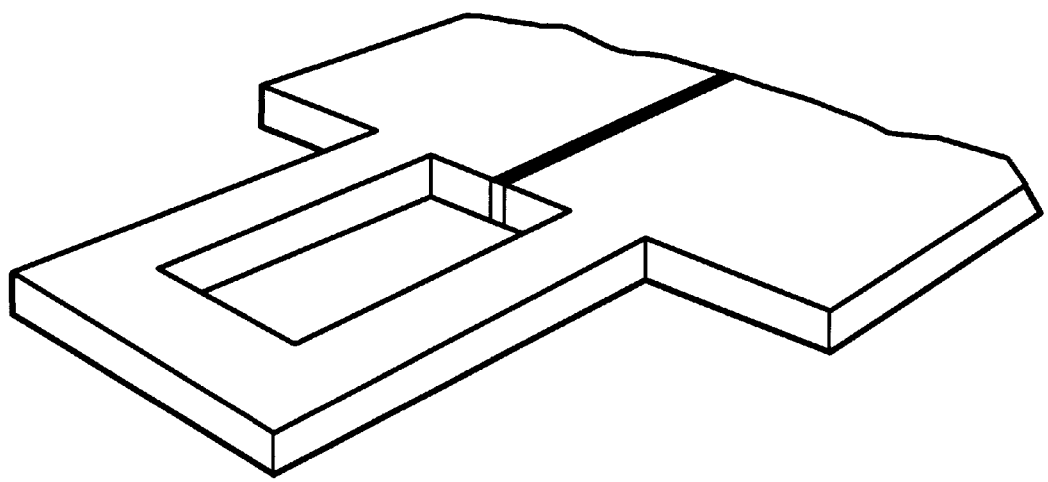
FIG. 5 is a block diagram of a cantilever that can be heated by passing current through the cantilevers.

This invention further contemplates a sensor device that can be regenerated by heating the cantilever such as by passing the current through the cantilever as shown in FIG. 5. Since the cantilever has a very small thermal mass it can be heated to hundreds of degrees centigrade in a fraction of a second and cooled quickly.

Currently, most microcantilevers are made out of silicon or silicon nitride. However, these microcantilevers may be made out of large band gap semiconducting material such as ZnO or TiO2. They may also be made out of other semiconducting materials that do not have an oxide layer on the surface. Such cantilever materials, therefore, have well defined energy bands that extend up to the surface. When the molecules of analyte are adsorbed on the surface of these materials they form surface states that have well defined levels with respect to the energy bands of the material. Depending on the Fermi level of the material these surface states can be filled or empty. If there is more than one analyte present in the sampling medium, different chemical species will form different surface states with respect to the Fermi level of the substrate material. Therefore, the surface states induced by particular adsorbates are unique in energy with respect to the energy bands of the specific semiconductor.

These adsorption-induced surface states can be optically activated by photons of appropriate energy. Optical activation can be either by removing the electrons from a filled surface state into conduction band or by filling the empty surface states by electrons from the valence band. Experimentally, this can be achieved by shining a beam of light and continuously varying its wavelength from near valence band edge to conduction band edge. In this method a beam of photon is used to change the population density of the surface states. FIG. 1 illustrates an apparatus for making the measurement.

As shown in FIG. 1, a monochromater with a frequency scanner or filter 1 is used to shine a light 3 onto a mirror 5 which may or may not have a diffraction grating cut into it. The reflected light 7 is shone upon a cantilever 9 mounted on a base 10. In the presence of an adsorbate 11, the cantilever is bent, and the bending is detected when a light beam 13 from laser diode 15 is reflected from the bottom of cantilever 9 and detected by position sensitive detection 17.

FIG. 2 illustrates energetically the surface states which are being used to produce the detectable signal. $E_c$ is the conduction band. $E_v$ is the valence band. $E_s$ is the energy of the surface states. The energy difference between the valance band and the conduction band at the edge is the band gap. $E_f$ is the Fermi energy. At the surface of the cantilever, the dangling bonds described above cause distortion of the bulk energy levels as illustrated. When an adsorbate is received on the surface, the adsorbate adopts its own energy states which may be perturbed when photons having energy $E_c$–$E_s$ are impinged on it. Charge carriers enter the conduction band and the change in stress is revealed by a bending of the cantilever.

When the cantilever is bent, the changes are detected by position sensitive detector 17. FIG. 3 is a plot of cantilever bending vs. wave length of the impinged light and serves as a chemical fingerprint.

The change in wavelength of the light can be achieved by a number of ways such as by utilizing a monochromator and a white light source with sub-bandgap wavelength. Filters may be utilized so as to limit the wavelengths to sub-bandgap region. If the energy position corresponding to a particular analyte is known, alternatively, photodiode or diode laser along with filters can be used to identify the analyte, i.e., the device becomes a detector specific to an analyte. Finally, a few cantilevers, each illuminated with a different wavelength, can be used to avoid scanning the wavelength using a monochromator. Different wavelength from a dispersing source such as a prism, lens, or a grating, can be used.

The microcantilevers may be micromachined using large band semiconductors. It is also possible to make the microcantilevers out of conventional base materials such as silicon and then growing a high quality film of desired large band gap semiconducting material on the top of that. This approach will be useful when array approaches are considered for production of commercial instruments.

One way to measure microcantilever bending is by using an optical technique. In this technique, cantilever bending is recorded by light deflection from the tip of the cantilever into a photodetector [position sensitive detector, (PSD)]. The d.c. variation in the PSD corresponds to the bending of the cantilever.

Other techniques of detecting cantilever movement such as piezoelectric, piezoresistive, capacitive, electron tunneling, magnetic, and electrical techniques also can be used to detect cantilever motion.

The bending of the cantilever is recorded as a function of photon energy. A reference cantilever may be used for differential measurements. The differential deflection of the cantilever as a function of photon energy represents the energy levels of the adsorbed molecules. FIG. 4 illustrates an array of cantilevers including reference cantilevers. The distance between the peaks in the spectrum with respect to the conduction or valence band represent its energy and the height of the peak is proportional to the amount of adsorbate. In addition to the energy location of the adsorbate, rise time and decay time may be used to uniquely identify the chemical.

The cantilevers can be fabricated in such a way that they can be heated up to several hundred degrees centigrade by passing a current through the cantilever. Because the thermal mass of the cantilever is so small, they can be heated and cooled in milliseconds. Heating the cantilever desorbs the adsorbates from the surface, regenerating the cantilever sensor. In this way, the instruments can be rezeroed quickly in the field.

There are many different embodiments encompassed by this invention. All embodiments involve a cantilever or an array of cantilevers, a means to expose the cantilever to analyte or mixtures of analytes, a means of illuminating one surface of the cantilever modified by the adsorbate using a light source whose energy can be varied in a controlled fashion, a means to detect the cantilever motion as a function of the energy of irradiating photon.

EXAMPLE 1

A microcantilever is designed in such a way that it undergoes bending due to variation in the surface state charge due to photon-induced changes in the population. Recording the microcantilever bending as a function of the wavelength of the exciting light will show peaks belonging to the surface states akin to an optical spectrum. The energy of this spectrograph can be calibrated with respect to the valence and conduction band of the substrate material.

EXAMPLE 2

The cantilever as described in Example 1 is exposed to an analyte or combination of analytes. The cantilever is then irradiated with pulses of photons whose energy changes in a discrete fashion. In addition to scanning the energy of the photons (changing the wavelength), the photon source is also pulsed with a frequency such that the cantilever responds to the pulse by bending as in the case of photo-thermal excitation or photo-mechanical excitation. The photon pulse shape and the frequency is such that the cantilever does not go into resonance. This can be achieved by using sinusoidal pulses whose frequency is far away from the natural resonance frequency of the cantilever or its overtones.

The irradiating photons either populate or depopulate the surface states. At the end of the pulse, when no more photons are impinging on the surface, the cantilever returns to equilibrium position.

The rate at which the cantilever returns to equilibrium position depends on the trapped charge carriers in the surface states and its energy location and distribution. The variation in the rate of cantilever return to equilibrium position with respect to a reference cantilever as a function of photon energy may be used to uniquely identifying the molecule.

In some cases the surface states may be electrically isolated in such a way that the trapped charges have a long life-time. In such cases irradiation with another pulse of higher energy photons immediately following irradiation with probing photons (photons whose energy is varies) can be used to depopulate the surface states.

EXAMPLE 3

Another embodiment using this concept may involve exciting the cantilevers with rectangular or square light pulses such that the cantilever goes into resonance. As the cantilevers are made of noncentrosymmetric materials such as ZnO, GaAs, etc which show piezoelectric effect, bending results from accumulation of charges on the surface. Therefore, the surface states are populated and depopulated during each oscillation. The extent of populating or depopulating depends on the wavelength of exciting photon. Therefore, the amplitude of the oscillation will change depending on the population of the surface states.

EXAMPLE 4

A plurality of cantilevers fabricated from a common substrate may be coated with different wide band gap materials. The bending or resonance response of the cantilevers as a function of photon energy will be unique for each cantilever element due to different positions of the energy levels (here it is required that all the cantilevers are electrically isolated from each other). Spectral signatures from multiple cantilevers may now be used for distinguishing analytes. As a result the resonance response of an array of cantilevers using different noncentrosymmetric material will uniquely identify the analyte.

EXAMPLE 5

The microcantilever may be excited into resonance by external means such as piezoelectric, magnetic, electrostatic, or acoustic methods. For example, the cantilever may be excited into resonance by scanning the frequency of the a.c. voltage applied to the piezoelectric cantilever holder. The maximum amplitude of the vibration represents the resonance frequency. The amplitude of the cantilever vibration changes when exposed to light due to excitation of surface states. The amplitude versus wavelength spectrum shows position of surface states introduced by adsorption of analytes.

The examples above are illustrative of the invention but do not limit the scope of this disclosure. Changes which may be obvious to those skilled in the art are included within the scope of this invention as defined by the claims following.

What is claimed is:

1. A method of chemical sensing using the adsorption-induced surface states on a semiconductor cantilever comprising:

exposing a surface of a semiconductor cantilever to an analyte;

irradiating the exposed surface of a microcantilever with discrete wavelengths of light;

measuring the deflection of the cantilever caused by the variation in the surface state population of charge carriers;

mapping the cantilever deflection as a function of the energy of the illuminating photons.

2. A method according to claim 1, wherein the cantilever is made of semiconductor materials selected from a group consisting of ZnO, GaAs, CdSe, CdS, GaP, SiC, TiO2 and SnO2.

3. A method according to claim 1, wherein the said illuminating light source consists of a variable monochromatic light source.

4. A method according to claim 1, wherein the cantilever element is modified by an inert material at the opposite side such that exposing to an analyte or combination of analytes changes the surface state density of the semiconductor surface only on one surface.

5. The method according to claim 1, wherein said cantilever deflection measuring step consists of optical, piezoresistive, piezoelectric, capacitive, or electron tunneling means.

6. A method according to claim 1 wherein sensing element is a plurality of cantilevers.

7. A method according to claim 3 wherein the irradiating light source is pulsed.

8. A method according to claim 7, wherein the deflection of the cantilever which is noted is the amplitude of vibration.

9. A method according to claim 1 wherein the radiating step consists of increasing the level of said photon energies in discrete amounts.

10. A method of sensing according to claim 1 further comprising a reference cantilever.

11. A method according to claim 6 wherein each member in the plurality of cantilevers having identical surfaces is exposed to radiation with different wavelength using a dispersing element and noting the deflections of the cantilever members.

12. A method according to claim 11 wherein each member of the plurality of the cantilevers has a different semiconducting element.

* * * * *